(12) United States Patent
Fortin et al.

(10) Patent No.: US 10,159,577 B2
(45) Date of Patent: Dec. 25, 2018

(54) DYNAMIC CERVICAL DISK PROSTHESIS PROVIDED WITH DAMPING

(71) Applicant: BIOSPINE IMPLANTS, Pessac (FR)

(72) Inventors: Frederic Fortin, Pessac (FR); Johann Robin, Begles (FR); Brice Sennequier, Pessac (FR)

(73) Assignee: BIOSPINE IMPLANTS, Pessac (FR)

( * ) Notice: Subject to any disclaimer, the term of this patent is extended or adjusted under 35 U.S.C. 154(b) by 543 days.

(21) Appl. No.: 14/426,844

(22) PCT Filed: Sep. 4, 2013

(86) PCT No.: PCT/FR2013/000228
§ 371 (c)(1),
(2) Date: Mar. 9, 2015

(87) PCT Pub. No.: WO2014/041256
PCT Pub. Date: Mar. 20, 2014

(65) Prior Publication Data
US 2015/0245917 A1 Sep. 3, 2015

(30) Foreign Application Priority Data
Sep. 11, 2012 (FR) ..................... 12 02407

(51) Int. Cl.
*A61F 2/44* (2006.01)
*A61F 2/30* (2006.01)

(52) U.S. Cl.
CPC ............. *A61F 2/442* (2013.01); *A61F 2/4425* (2013.01); *A61F 2002/30367* (2013.01);
(Continued)

(58) Field of Classification Search
CPC .................. A61F 2002/443; A61F 2/4425
See application file for complete search history.

(56) References Cited

U.S. PATENT DOCUMENTS

| 6,582,468 B1 | 6/2003 | Gauchet |
| 2005/0197703 A1 | 9/2005 | Diaz et al. |

(Continued)

FOREIGN PATENT DOCUMENTS

| FR | 2 787 015 | 6/2000 |
| WO | 2005 084385 | 9/2005 |

(Continued)

OTHER PUBLICATIONS

International Search Report dated Dec. 18, 2013 in PCT/FR13/000228 Filed Sep. 4, 2013.

*Primary Examiner* — Olivia C Chang
(74) *Attorney, Agent, or Firm* — Oblon, McClelland, Maier & Neustadt, L.L.P.

(57) ABSTRACT

The invention relates to a dynamic cervical disk prosthesis (1) comprising two upper (11) and lower (12) rigid plates containing a viscoelastic element (10), said upper and lower plates (11 and 12) having a slightly cambered and striated contact face, the main characteristic of this invention being that the lower plate (12) is in the form of a housing, compatible with a twist-lock of the upper plate (11) while allowing the mobility and damping of the two plates (11 and 12) around the viscoelastic element (10) that can be freely distorted thereby avoiding all risk of detachment of the prosthesis when subjected to applied forces.

6 Claims, 5 Drawing Sheets

Figure 1:
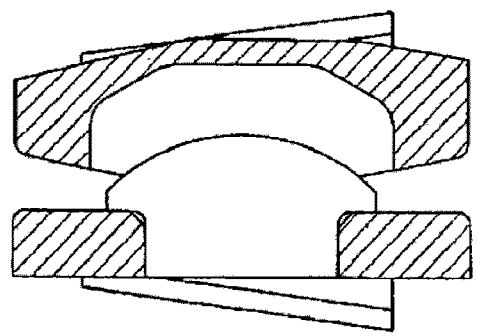

(52) U.S. Cl.
CPC ............ *A61F 2002/30393* (2013.01); *A61F 2002/30563* (2013.01); *A61F 2002/30649* (2013.01); *A61F 2002/30662* (2013.01); *A61F 2002/30825* (2013.01); *A61F 2002/30827* (2013.01); *A61F 2002/30904* (2013.01); *A61F 2002/443* (2013.01)

(56) References Cited

U.S. PATENT DOCUMENTS

| | | |
|---|---|---|
| 2005/0197704 A1 | 9/2005 | Diaz et al. |
| 2006/0142862 A1* | 6/2006 | Diaz ............... A61F 2/4611 623/17.13 |
| 2006/0241768 A1 | 10/2006 | Trieu |
| 2007/0135922 A1 | 4/2007 | Trieu |
| 2008/0046083 A1* | 2/2008 | Hewko ............ A61F 2/4425 623/17.16 |
| 2011/0082552 A1 | 4/2011 | Wistrom et al. |

FOREIGN PATENT DOCUMENTS

| | | |
|---|---|---|
| WO | 2005 084386 | 9/2005 |
| WO | 2008 094260 | 8/2008 |
| WO | 2010 126915 | 11/2010 |

* cited by examiner

DYNAMIC CERVICAL DISK PROSTHESIS PROVIDED WITH DAMPING

FIELD OF THE INVENTION

The invention is a dynamic cervical disk prosthesis provided with damping which is inserted between the cervical vertebrae by way of replacement of the deteriorated intervertebral disk.

PRIOR ART

In the prior art there exist documents that propose cervical disk prostheses which more often than not are an assembly of rigid means and in this case damping is absent and wear-generating friction occurs rapidly and the desired anatomical functions no longer are present. In this way patent No. FR2895234 describes and claims such a prosthesis that does not possess any flexibility function or necessary damping.

Patent FR2929105 describes a device one of the elements of which comprises two parts independent of one another at least one of which includes an articular surface and each of the two parts comprising an articular seat delimited by a curved wall; the said element comprises a ring in the form of an O-ring made of elastically deformable material and one of the said seats is dimensioned so as to accommodate a part radially outside of this ring while the other seat is dimensioned to accommodate a part radially inside this ring. The functions of this device are complex. In effect, there is a combination translation, rotation movement and swivel movement with damping, this by virtue of the O-ring that is elastically deformable. This O-ring the cross-section diameter of which is less than one millimeter seems underdimensioned in relation to the level of load that the vertebrae impose thereon. In addition, the complex translation movements are conducive to vertebral displacements which could bring about spondylolisthesis. This invention of the prior art therefore carries risks of fragility and inadequacy with the pathologies that it is supposed to treat.

Patent WO2012047279 describes a device comprising two rigid plates between which there is placed a deformable core made of viscoelastic material, surrounded by an annular fibrous structure connected to the two plates, itself surrounded by a protective membrane. In comparison with the invention of patent FR2929105, the damping is improved by virtue of a significant increase in the quantity of viscoelastic material which makes it possible to come closer to the behavior of a healthy intervertebral cervical disk. Nevertheless, the great variety of flexible materials and the considerable number of supple components that make up the device may induce parasitic shearing movements potentially harmful for the patient and possibly compromising the life of the prosthesis. In addition, the complexity of the assembly creates a high production cost which is an indication of absence of inventive activity.

The present invention avoids the complexity by selecting a method of deformation without parasitic constraint of the viscoelastic element which is one of the basic risks that must be eliminated in order to ensure a dynamic functioning with damping of the device in the long term. So as to reduce the risks noted above, the present invention combines a swivel-type movement with an optimized damping while limiting the number of means, and allowing the central viscoelastic means to deform freely during the forces that it undergoes.

The Figures serving for understanding of the invention are the following:

FIG. 1—plate 1/5, view in cross-section of the device described and claimed in patent FR2895234 (Prior art)

Figure 2:
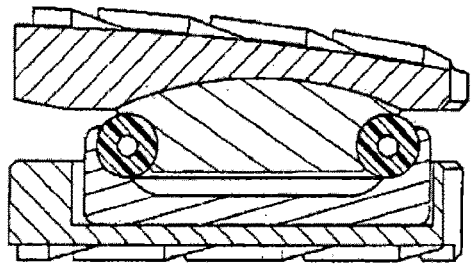

FIG. 2—plate 1/5, view in cross-section of the device described and claimed in patent FR2929105 (Prior art)

Figure 3:
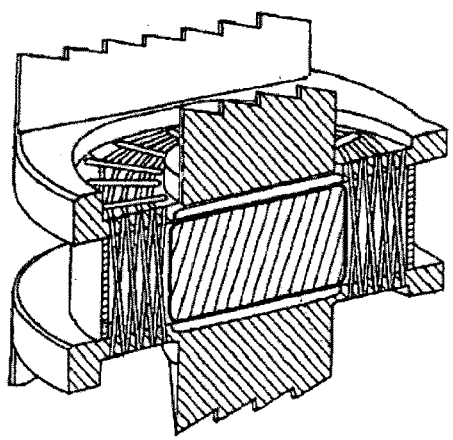

FIG. 3—plate 1/5, view in cross-section of the device described and claimed in patent WO2012047279 (Prior art)

Figures 4, 5:
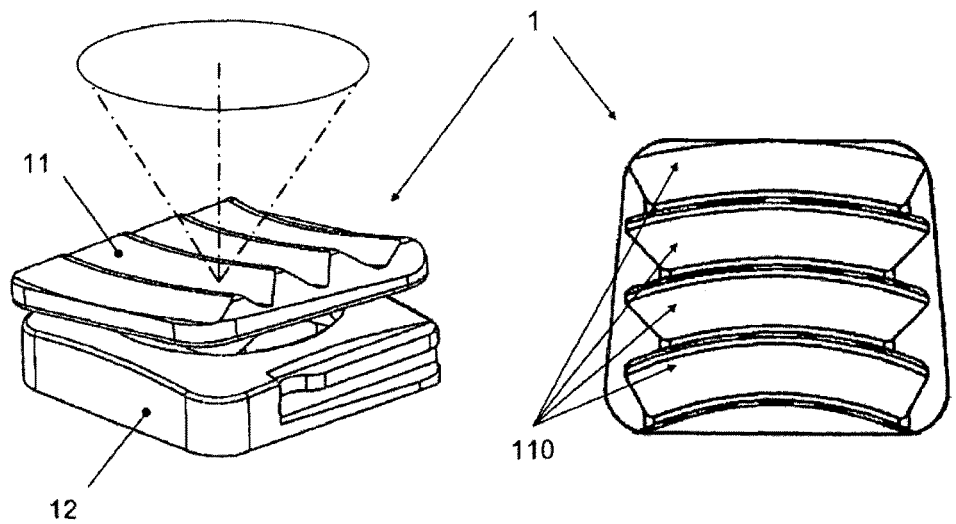
Figures 6, 7:
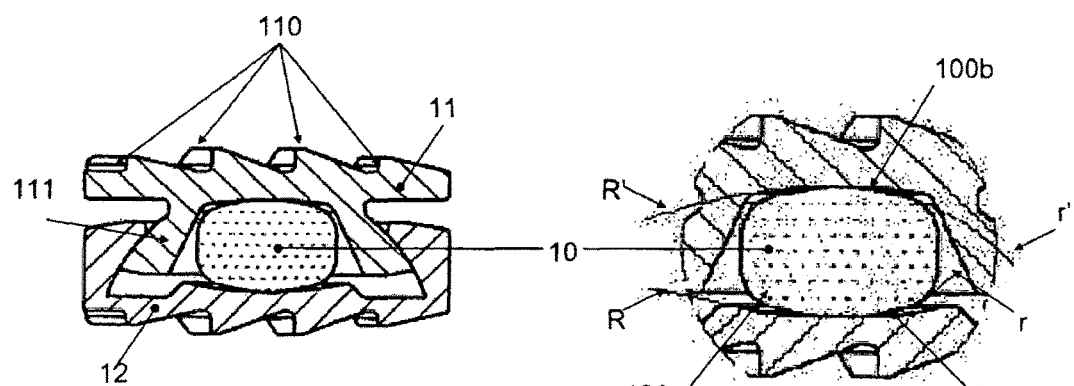
Figure 8:
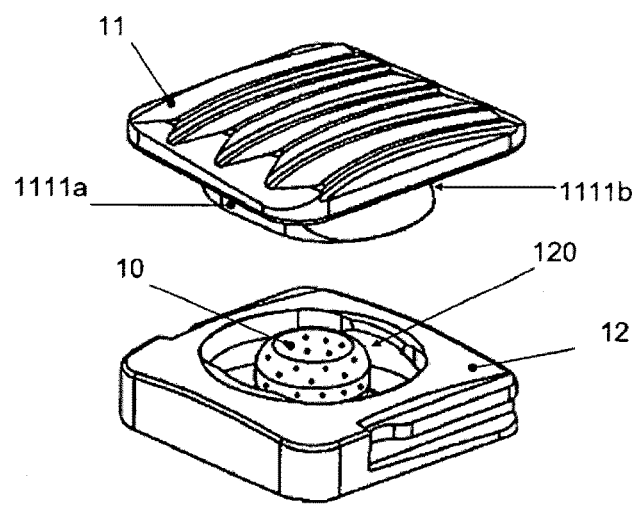
Figure 9:
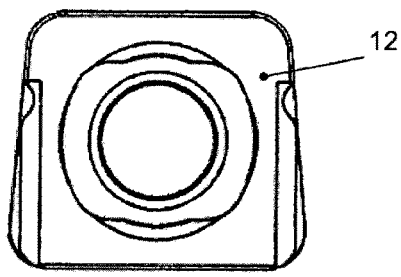
Figure 10:
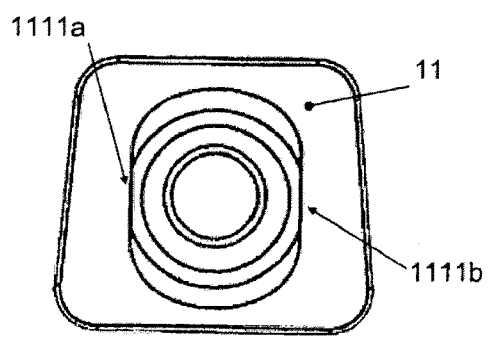
Figure 11:
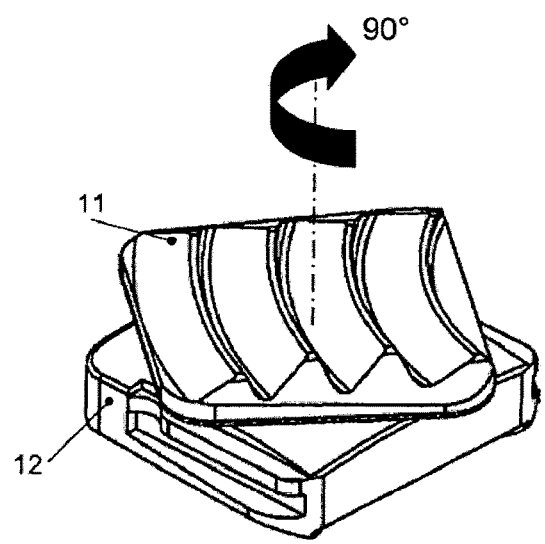
Figure 12:
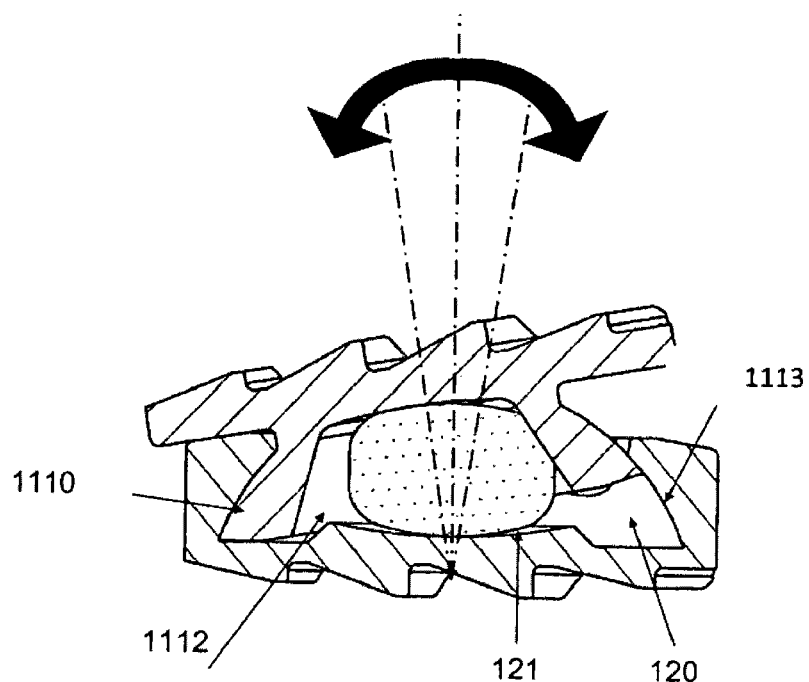
Figure 13:
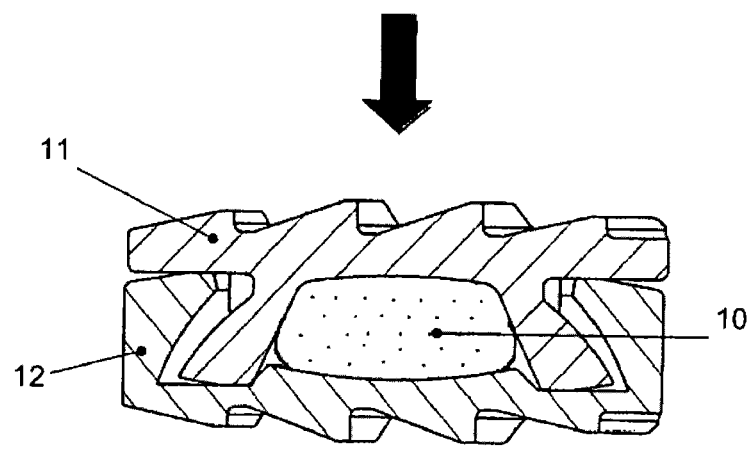
Figure 14:
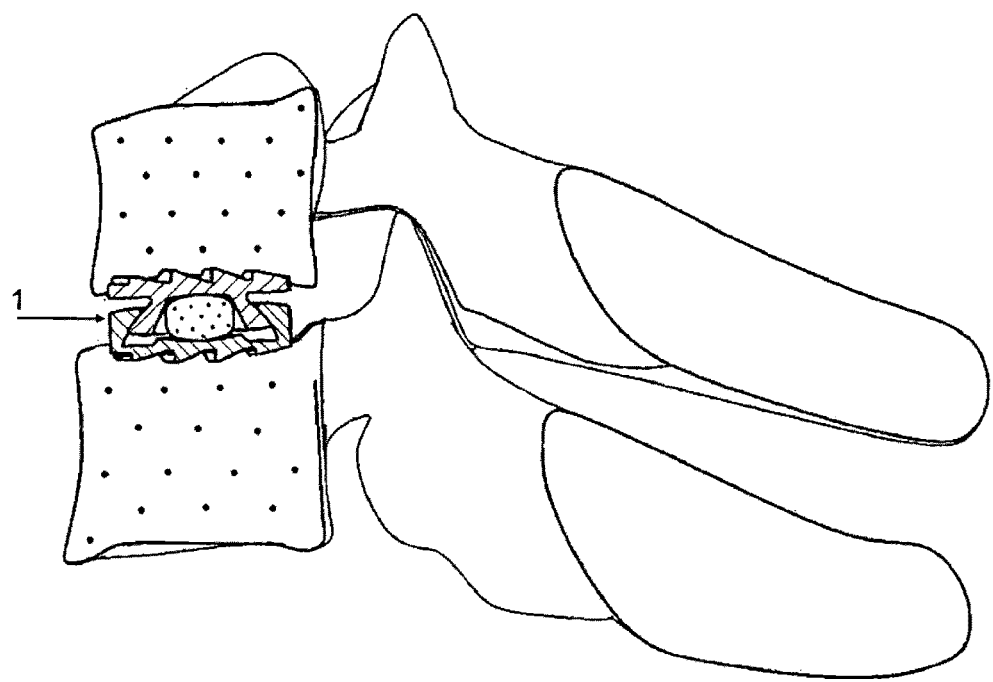
Figure 15:
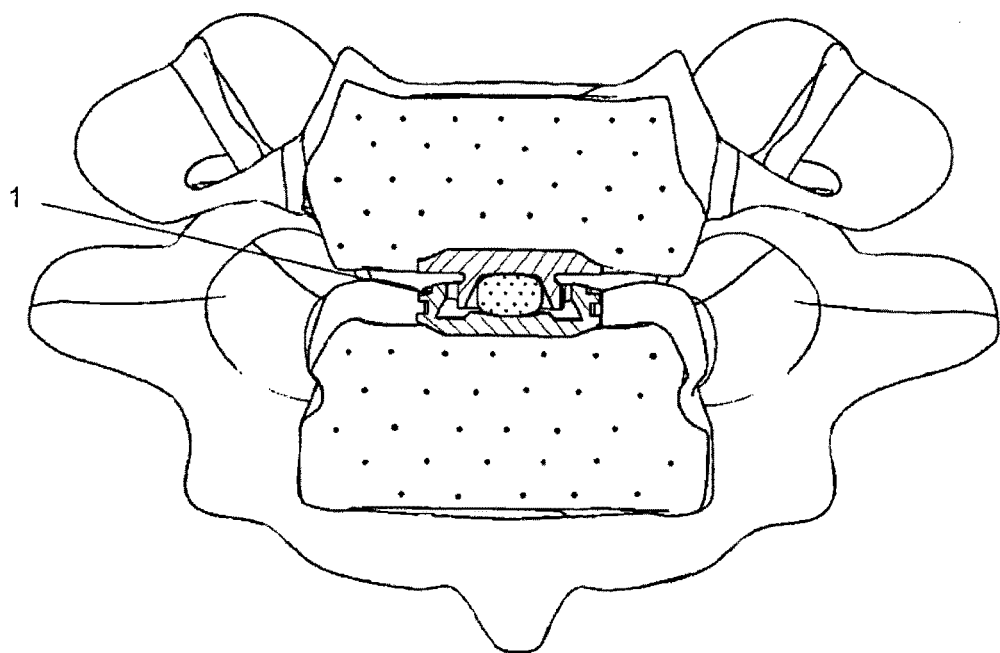

FIG. 4—plate 2/5, perspective view of the device representing the dynamic cervical disk prosthesis FIG. 5—plate 2/5, view from above of the device representing the dynamic cervical disk prosthesis FIG. 6—plate 2/5, view in cross-section of the device representing the dynamic cervical disk prosthesis FIG. 7—plate 2/5, detail view in cross-section of the device showing the dynamic cervical disk prosthesis with its central viscoelastic element FIG. 8—plate 3/5, semi-exploded perspective view of the dynamic cervical disk prosthesis showing the entirety of these means FIG. 9—plate 3/5, view from above showing the specific form of the lower plate ready to accommodate the upper plate of the dynamic cervical disk prosthesis FIG. 10—plate 3/5, view from above showing the specific form of the upper plate ready to be inserted into the lower plate of the dynamic cervical disk prosthesis FIG. 11—plate 3/5, perspective view of the dynamic cervical disk prosthesis in the process of locking FIG. 12—plate 4/5, view in cross-section showing the dynamic cervical disk prosthesis in flexion-extension working mode FIG. 13—plate 4/5, view in cross section showing the dynamic cervical disk prosthesis in compression working mode FIG. 14—plate 5/5, profile view in cross-section of the dynamic cervical disk prosthesis assembled between two vertebrae FIG. 15—plate 5/5, front view of the dynamic cervical disk prosthesis assembled between two vertebrae Dynamic cervical disk prosthesis 1 comprises two upper 11 and lower 12 rigid plates holding a viscoelastic element 10.

Upper 11 and lower 12 plates possess a striated and slightly cambered contact face so as to follow perfectly the concavity of the vertebral bodies and allow a good hooking-on. Striae 110 (FIG. 5) possess a curvilinear sawtooth profile making it possible to be impacted by pressure into the bone and in this way preventing any expulsion of the prosthesis out of its housing. This sawtooth profile follows a curvilinear extrusion which makes it possible to generate a good hooking-on over the entire surface thereof and facilitates the installation of the prosthesis, which imparts a great stability to the prosthesis.

The internal part of upper plate 11 has a circular arch form 111 (FIG. 6) in the vertical plane, its outer face 1110 (FIG. 12) possesses a spherical geometry which, on the outer edge possesses two diametrically opposed planes 1111a and b allowing the introduction of viscoelastic element 10 into lower plate 12 then locking by rotation of a quarter turn of upper plate 11 in lower plate 12.

The bottom of lower plate 12 comprises a concave base 121 and forms with circular arch 111 of upper plate 11 a cavity 1112 containing viscoelastic means 10 in order to allow it to be deformed without loss of volume or constraint which makes it possible to damp the applied forces.

Cavity 1112 has a form of revolution adapted to the deformation of viscoelastic means 10. Lower plate 12 in the form of a housing accommodates lower part 111 of upper plate 11, by virtue of forms specially designed for fitting together, the said forms being paired with those of upper plate 11. In effect, lower plate 12 possesses an opening 120 (FIGS. 8 and 12) which allows insertion of upper plate 11 into lower plate 12, then locking thereof by a quarter turn. This technique of assembly by rotation of a quarter turn of upper plate 11 in lower plate 12 makes prosthesis 1 incapable of being dismantled once in place by preventing any detachment of the two plates 11 and 12 in contact with the vertebrae.

More precisely, lower plate 12 in the form of a housing has internal walls with spherical geometry 1113 which are paired, apart from the assembly clearances, to spherical geometry 1110 of means 111, which makes it possible to generate a swivel movement with a minimum of friction, very well adapted to the forces exerted by the spinal column at the cervical level.

The bottom of lower plate 12 comprises a concave base 121 (FIGS. 7 and 12) on which viscoelastic means 10 rests. Central viscoelastic element 10 possesses a form of revolution with cambered upper and lower faces 100a and b with radii r and r' (FIG. 7). Base 121 of lower plate 12 possesses a concave face with radius R (FIG. 7) greater than radius r of lower cambered face 100a of viscoelastic means 10. Likewise circular arch 111 of upper plate 11 possesses a radius of curvature R' (FIG. 7) greater than radius r' of cambered upper face 100b of viscoelastic means 10, these forms having been specifically designed to auto-center viscoelastic means (10) on concave base (121) of lower plate (12) and to create spaces allowing viscoelastic means 10 to be deformed freely in any direction without loss of volume or concentration of constraints at the time of applied forces.

Without the conceiving of these geometries specifically designed and concerning means described above, and then the experiments performed, in order to verify that these functions indeed were achieved, the risk of concentration of constraints on viscoelastic means (10) would be considerable, therefore harmful for the life of prosthesis 1.

Once assembled, prosthesis 1 performs as a swivel by virtue of the combination of the means described above. This swivel movement is accompanied by flexion-extension and rotation movements of plates 11 and 12 integral with the vertebrae between which prosthesis 1 is inserted.

Central viscoelastic means 10, because of the physico-chemical characteristics of the polymer which constitutes it, provides a protective damping to prosthesis 1 during mechanical forces in compression and flexion-extension respecting the anatomical behavior of a healthy intervertebral disk.

At the time of extreme mechanical forces, upper plate 11 comes into contact with the bottom or the top of lower plate 12 (FIG. 13), which constitutes a safety stop whatever the intensity and direction of the mechanical force, in this way avoiding any damaging of the prosthesis.

Because of the configuration and the combination of its various means, prosthesis 1 guarantees the patient a functioning perfectly adapted to the biomechanics of the spinal column with an optimal life.

The invention claimed is:

1. A dynamic cervical disk prosthesis comprising:
   an upper rigid plate and a lower rigid plate, said upper rigid plate and said lower rigid plate defining a central cavity holding a viscoelastic element, each of the upper rigid plate and the lower rigid plate comprising a slightly cambered and striated outer, bone-contacting face,
   wherein the lower rigid plate has a housing form compatible with a locking of the upper rigid plate onto the lower rigid plate by rotation of the upper rigid plate, while allowing mobility and damping of the upper rigid plate and the lower rigid plate around the viscoelastic element in a locking position, in this way avoiding any risk of detachment of the upper rigid plate from the lower rigid plate of the prosthesis subjected to forces, and wherein said central cavity has a size larger than the size of said viscoelastic element allowing said viscoelastic element to be deformed inside said central cavity.

2. The dynamic cervical disk prosthesis according to claim 1, wherein an internal part of the upper rigid plate has a circular arch form in the vertical plane, an outer face of the circular arch form comprising a spherical geometry which, on the outer edge possesses two diametrically opposed planes allowing an introduction of the viscoelastic element into the lower rigid plate then a locking by rotation of a quarter turn of the upper rigid plate in the lower plate which avoids unlocking of the prosthesis.

3. The dynamic cervical disk prosthesis according to claim 2, wherein the lower rigid plate comprises internal walls with a spherical geometry complementarily paired to the spherical geometry of the outer face of the circular arch form in order to generate a swivel movement between the two plates with a minimum of friction.

4. The dynamic cervical disk prosthesis according to claim 2, wherein a concave base of an inner surface of the lower rigid plate forms, with the circular arch form of the upper rigid plate, the central cavity, said central cavity containing the viscoelastic element allowing the viscoelastic element to be deformed without loss of volume or constraint inside the central cavity, thereby making it possible to damp the applied forces.

5. The dynamic cervical disk prosthesis according to claim 4, wherein a concave face of the concave base has a radius R, the circular arch form having a radius R', and such that R and R' are always greater than radii r and r' of corresponding cambered contact faces of the viscoelastic element, these radii R, R', r, and r' having been specifically designed to auto-center the viscoelastic element on the concave base of the lower rigid plate and to create spaces allowing the viscoelastic element to be deformed freely.

6. The dynamic cervical disk prosthesis according to claim 1, wherein the upper rigid plate is adapted to come into contact with the bottom or the top of the lower rigid plate at the time of extreme mechanical forces, which constitutes a safety stop whatever the intensity and the direction of the mechanical force, in this way avoiding any damaging.

* * * * *